United States Patent [19]

Ito et al.

[11] Patent Number: 4,769,493

[45] Date of Patent: Sep. 6, 1988

[54] PROCESS FOR PRODUCING TETRAFLUOROPHTHALIC ACID

[75] Inventors: Haruaki Ito; Utaro Matsushita; Toshiaki Shimizu; Nobuo Ishikawa, all of Kanagawa; Masaaki Shimizu, Tokyo, all of Japan

[73] Assignee: SDS Biotech K.K., Tokyo, Japan

[21] Appl. No.: 85,498

[22] Filed: Aug. 14, 1987

[30] Foreign Application Priority Data

Aug. 18, 1986 [JP] Japan ............................... 61-191752
Dec. 25, 1986 [JP] Japan ............................... 61-307992

[51] Int. Cl.$^4$ .............................................. C07C 51/00
[52] U.S. Cl. ..................................... 562/480; 560/83; 562/483
[58] Field of Search ................... 562/480, 483; 560/83

[56] References Cited

U.S. PATENT DOCUMENTS 3,221,044 11/1965 Hoch .................................. 562/480
4,022,817 5/1977 Knobloch et al. ............... 562/480 X

FOREIGN PATENT DOCUMENTS 986892 3/1965 United Kingdom .

OTHER PUBLICATIONS

Chemical Abstracts, vol. 64, No. 10, May 9, 1966, 14124a–14125b.
Chemical Abstracts, vol. 85, No. 5, Aug. 2, 1976, 32584Q.

Primary Examiner—Werren B. Lone
Assistant Examiner—Vera C. Clarke
Attorney, Agent, or Firm—Sughrue, Mion, Zinn, Macpeak, and Seas

[57] ABSTRACT

A process for producing tetrafluorophthalic acid is disclosed, which comprises the steps of:

(a) reacting an alkali metal fluoride and at least one imide compound represented by formula (I) or (II)

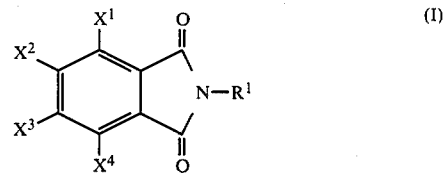

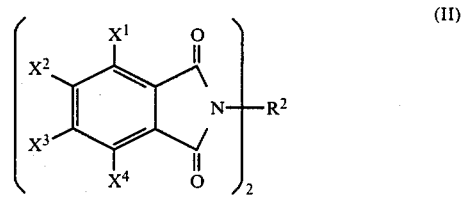

wherein $X^1$, $X^2$, $X^3$, and $X^4$, which may be the same or different, each represents a chloride atom or a bromine atom, $R^1$ represents a monovalent organic group, and $R^2$ represents a divalent organic group, to provide an N-substituted tetrafluorophthalimide; and (b) hydrolyzing the tetrafluorophthalimide in the presence of an acid.

26 Claims, No Drawings

PROCESS FOR PRODUCING TETRAFLUOROPHTHALIC ACID

FIELD OF THE INVENTION

This invention relates to a novel process for producing tetrafluorophthalic acid.

BACKGROUND OF THE INVENTION

Known processes for producing tetrafluorophthalic acid include (1) a process of fluorinating tetrachlorophthalonitrile and hydrolyzing tetrafluorophthalonitrile, as described in *Kogyo Kagaku Zasshi (Journal of Industrial Chemistry)*, 72, 447–448 (1970); and (2) a process of chlorinating tetrachlorophthalic anhydride, fluorinating the tetrachlorophthalic acid dichloride thus obtained, and then hydrolyzing the tetraflourophthalic acid difluoride, as described in *Zh. Obshabh. Khim.*, 36, 139 (1966).

However, the first process described above has the disadvantage that the phthalonitrile which is used as the starting material is hard to handle due to its high toxicity. Furthermore, the polymerization of phthalonitrile occurs during the synthesis of tetrachlorophthalonitrile by the vapor phase chlorination reaction of phthalonitrile, which reduces the yield and frequently inactivates the catalyst. For these reasons, it is difficult to use this process for the industrial production of tetrafluorophthalic acid. According to the description of *Organic Chlorine Compounds*, pages 490–493 (John Wiley Co., 1948), the second process described above is an uneconomical process, since tetrachlorophthalic acid dichloride is easily isomerized to form 3,3,4,5,6,7-hexachlorophthalide; the yield for the fluorination reaction of tetrachlorophthalic acid dichloride is low because of the isomerization reaction; and further the molar equivalent of the fluorination reagent required is 6 times that of tetrachlorophthalic acid dichloride.

The above-described processes have various disadvantages that prevent their practical use in industrial production processes.

SUMMARY OF THE INVENTION

An object of this invention is to provide an industrially advantageous process for producing tetrafluorophthalic acid.

As the result of various investigations, the inventors have discovered that tetrafluorophthalic acid can be advantageously produced on an industrial scale by the steps of (a) reacting at least one imide compound represented by the following formula (I) or (II) and an alkali metal fluoride to form a corresponding N-substituted tetrafluorophthalimide, and (b) hydrolyzing the tetrafluorophthalimide in the presence of an acid;

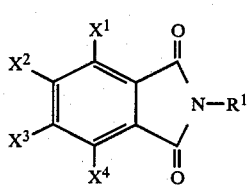

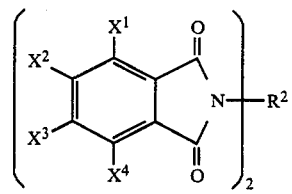

wherein $X^1$, $X^2$, $X^3$, and $X^4$, which may be the same or different, each represents a chlorine atom or a bromine atom, $R^1$ represents a monovalent organic group, and $R^2$ represents a divalent organic group.

DETAILED DESCRIPTION OF THE INVENTION

The imide compound represented by formula (I) or (II) described above, which is used as a starting material in the production process for tetraflorophthalic acid in this invention (both compounds hereinafter, are collectively referred to as "the imide compound") can be prepared by a known process as described, for example, in S. R. Sandler and W. Karo, *Organic Functional Group Preparation*, Vol. III, Chapter 7, pp. 241–267, Academic Press (1972). For instance, the imide compound can be obtained by a condensation reaction of an amine or diamine with a corresponding tetrahalophthalic anhydride, e.g., tetrachlorophthalic anhydride. This reaction sometimes forms amido acid as a reaction intermediate, depending upon the kind of solvent or reaction conditions such as reaction temperature used. When forming such a reaction intermediate, the reaction is performed in, for example, acetic anhydride using sodium acetate as a catalyst, whereby the cyclodehydration reaction proceeds with good yield to provide the imide compound represented by formula (I) or (II).

In formula (I) described above, preferred examples of the monovalent organic group represented by $R^1$ include a straight chain or branched chain alkyl group having from 1 to 8 carbon atoms, a cycloalkyl group having from 3 to 8 carbon atoms, an alkenyl group having from 3 to 8 carbon atoms, an aryl group such as a phenyl group and a naphthyl group, and a heterocyclic group which contains from 1 to 3 hetero atoms such as an oxygen atom, a nitrogen atom, and/or a sulfur atom and is a 5- or 6-membered ring which may form a condensed ring with an aromatic ring or a heterocyclic ring.

In formula (II) described above, preferred examples of the divalent organic group represented by $R^2$ include a straight chain or branched chain alkylene group having from 1 to 8 carbon atoms, a cycloalkylene group having from 3 to 8 carbon atoms, an alkenylene group having from 3 to 8 atoms, an arylene group such as an m- or p-phenylene group and a 1,4-naphthylene group, a divalent heterocyclic group which contains from 1 to 3 hetero atoms such as an oxygen atom, a nitrogen atom, and/or a sulfur atom and is a 5- or 6-membered ring which may form a condensed ring with an aromatic ring or a heterocyclic ring, and a group represented by -$R^3$-$R^4$-$R^5$-, wherein, $R^3$ and $R^5$ each represents a straight or branched chain alkylene group having from 1 to 8 carbon atoms, a cycloalkylene group having from 3 to 8 carbon atoms, and an alkenylene group having from 3 to 8 carbon atoms, and an arylene group such as an m- or p-phenylene group and a 1,4-naphthylene group, and a divalent heterocyclic group which contains from 1 to 3 hetero atoms such as an oxygen atom, a nitrogen atom, and/or a sulfur atom and is a 5- or 6-membered ring which may form a condensed ring with an aromatic ring or a heterocyclic ring, and $R^4$ represents those defined for $R^3$ and $R^5$ and further represents —O—, —S—, —SO—, —SO$_2$—, and

($R^6$: an alkyl group, a cycloalkyl group, an alkenyl group, an aryl group, or a heterocyclic group as defined for $R^1$), provided that all of $R^3$, $R^4$, and $R^5$ are not alkylene groups, cycloalkylene groups, alkenylene groups, or arylene groups.

Each of the groups represented by $R^1$ and $R^2$ may be substituted or unsubstituted, and the numbers of carbon atoms and the hetero atoms contained in the groups represented by $R^1$ to $R^6$ as set forth above do not include those of substituents if any. Examples of the substituent include a halogen atom, a straight or branched chain alkyl group having from 1 to 8 carbon atoms, a cycloalkyl group having from 3 to 8 carbon atoms, an alkenyl group having from 3 to 8 carbon atoms, an aryl group (e.g., a phenyl group and a naphthyl group), a heterocyclic group, a cyano group, a nitro group, $R^7O$—, $R^8S$—, $R^8SO$—, $R^8SO_2$—, and

wherein $R^7$, $R^8$, $R^9$, and $R^{10}$ each represents those defined for $R^1$. For example, $R^1$ may be an aralkyl group, an alkoxyalkyl group, or the like.

In a preferred embodiment of the imide compound represented by formula (I) or (II) described above, which is used in this invention, $R^1$ represents a methyl group, an ethyl group, a propyl group, an isopropyl group, a butyl group, an isobutyl group, a sec-butyl group, a tert-butyl group, a pentyl group, a hexyl group, a 2-ethylhexyl group, an octyl group, a cyclopentyl group, a cyclohexyl group, a benzyl group, a p-chlorobenzyl group, a p-methylbenzyl group, an allyl group, a phenyl group, a p-chlorophenyl group, a p-bromophenyl group, a p-fluorophenyl group, a p-tolyl group, a 2,4-dichlorophenyl group, a 3,4-dichlorophenyl group, a 2-chloro-4-methylphenyl group, a 2,4-xylyl group, a p-ethoxyphenyl group, an m-methylthiophenyl group, a p-(p-chlorophenoxy)phenyl group, a p-(benzenesulfonyl)phenyl group, a 1-naphthy group, a 2-naphthyl group, a 2-thienyl group, a 2-methoxyethyl group, a 2-(dimethylamino)ethyl group, a 3-[4-(dimethylamino)-phenyl]propyl group, a (3,5-dimethyl-4-isoxazolyl)-methyl group, a 3-(4-methoxyphenyl)butyl group, a 3-(4-methoxyphenyl)propyl group, a 6-methyl-2-pyridyl group, a 4-methoxy-2-methylphenyl group, a 3-methoxypropyl group, a 1-methyl-2-phenylethyl group, a 2,3,5,6-tetrafluoro-4-pyridyl group, a 2-phenoxyethyl group, a 4-nitrophenyl group, a 4-cyanophenyl group, a 2,6-dimethyl-4-pyrimidyl group, a 2-morpholinoethyl group, an α,α,α-trifluoro-o-tolyl group, a 2-(2-pyridyl)ethyl group, and a 3-pyridyl group; $R^2$ represents —CH$_2$CH$_2$—,

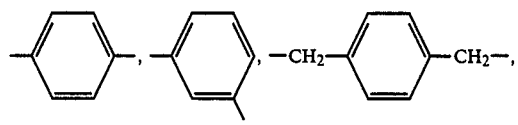
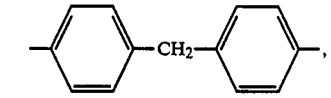
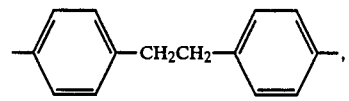
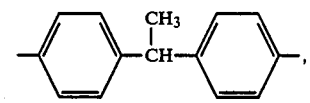
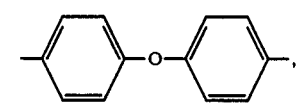
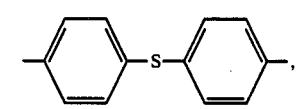
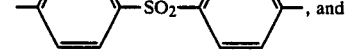
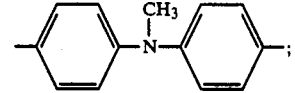

and $X^1$ to $X^4$ all represent a chlorine atom or all represent a bromine atom. However, the imide compound for use in this invention is not to be construed as being limited to these embodiments.

The process of this invention is now explained in greater detail.

The process of this invention includes a first step of synthesizing a corresponding N-substituted tetrafluorophthalimide by a fluorination reaction of the imide compound represented by formula (I) or (II) described above, and a subsequent step of synthesizing tetrafluorophthalic acid by the hydrolysis of the N-substituted tetrafluorophthalimide.

The first step can be performed in the presence or absence of a solvent. When using a solvent, an aprotic polar solvent such as dimethylformamide, dimethylsulfoxide, sulfolane and N-methyl-2-pyrrolidone is preferably used. The reaction temperature is generally in the range of from room temperature to about 250° C. If the reaction temperature is low, the reaction rate is slow and the reaction time is long, while if the reaction temperature is high, the formation of by-products such as tar components tends to be increased. For this reason, the reaction temperature is preferably in the range of from about 80° to 220° C., and more preferably in the range of from about 120° to 220° C.

As a fluorinating agent used in the first step, an alkali metal fluoride such as cesium fluoride, rubidium fluoride, potassium fluoride, sodium fluoride, ammonium fluoride and lithium fluoride is used, and potassium fluoride is particularly preferred. The amount of the alkali metal fluoride depends upon the imide compound and the alkali metal fluoride but is generally from about 4.0 to 12.0 mols per mol of the simple imide compound represented by formula (I). Accordingly, when using a bis-compound represented by formula (II) as the imide compound, the amount of the alkali metal fluoride is properly from about 8.0 to 24.0 mols per mol of the imide compound. Also, when potassium fluoride is used as the alkali metal fluoride, it is preferred that the amount thereof be from about 4.1 to 8.0 mols per mol of the simple imide compound and from about 8.2 to 16.0 mols per mol of the bis-compound.

The reaction time for the first step depends upon the fluorinating agent and solvent used, and the reaction temperature, but it is generally from about 0.2 to 72 hours, preferably from about 0.5 to 36 hours, and more preferably from about 0.5 to 10 hours.

In addition, the reaction rate can be advantageously increased by the addition of a phase transfer catalyst. Suitable catalysts include, for example, quaternary ammonium salts, quaternary phosphonium salts, and cyclic polyethers (a so-called "Crown ether"). The amount of the catalyst is from about 0.00001 to 0.6 mol, and preferably from about 0.001 to 0.3 mol per mol of the imide compound. It is preferred that the catalyst be added in a large amount in the above range when the imide compound is the bis-compound. Specific examples of the catalyst include tetraalkylammonium halides, tetraalkylammonium tetrafluoroborates, tetraalkylammonium phosphorustetrafluorides, alkyltriphenylphosphonium halides, tetraphenylphosphonium halides, 18-crown-6, dibenzo-18-crown-6, and dicyclohexano-crown-6, although the catalyst for use in this invention is not limited to these materials.

The second step is performed under acidic conditions. The reaction is usually conducted under heating, but can be generally performed in the range of from about room temperature to 200° C. but below a refluxing temperature, and is preferably not lower than about 70° C. Also, if desired, the reaction can be performed in a temperature range of from about 110° to 200° C. under a pressure of from about 1 to 15 kg/cm$^2$.

As the acid used in the second step, organic acids or inorganic acids are used, and mineral acids such as sulfuric acid, hydrochloric acid and phosphoric acid are preferably used.

The reaction time for the second step depends upon the reaction temperature, the kind and concentration of an acid, and the reaction pressure, but is usually from about 0.5 to 72 hours, and preferably from about 0.5 to 36 hours. The amount of the acid varies according to the reaction condition, but is usually from about 0.5 to 48 mols per mol of the N-substituted tetrafluorophthalimide. It is preferred that the acid be added in a large amount within the above range when the N-substituted tetrafluorophthalimide is the bis-compound (corresponding to the imide compound of formula (II)).

The concentration of the acid depends upon the kind of acid used. For example, in the case of using sulfuric acid as the acid, the concentration thereof is from about 30 to 98 wt %.

Also, the reaction can be performed using a proper solvent such as, for example, acetic acid, to prevent adhesion of fluorination products to the wall of the reaction vessel.

In the second step, high-purity tetrafluorophthalic acid can be obtained by first isolating tetrafluorophthalic anhydride formed as a reaction intermediate, or separating the product in solution from the reaction system, and hydrolyzing the product under acidic or neutral conditions, and this embodiment is particularly preferred. For example, by hydrolyzing the N-substituted tetrafluorophthalimide under acid conditions (e.g., H$_2$SO$_4$ concentration: from about 50 to 98%) and, after cooling, extracting the product with an aprotic solvent (e.g., toluene, benzene, chlorobenzene, xylene, etc.), a solution of tetrafluorophthalic anhydride can be obtained. Furthermore, by removing the solvent from the extract thus obtained, tetrafluorophthalic anhydride can be isolated. In this case, the tetrafluorophthalic anhydride may be purified by distillation, if desired, under a reduced pressure. Then, by hydrolyzing the tetrafluorophthalic anhydride thus obtained under acid or neutral conditions, tetrafluorophthalic acid can be obtained. In the hydration reaction, water is generally used in an amount of from 1 to 5000 mols per mol of the tetrafluorophthalic anhydride and the reaction temperature is usually from about 0° to 100° C. The reaction can be conducted by adding an acid (e.g., hydrochloric acid and sulfuric acid) as a catalyst. This technique of isolating tetrafluorophthalic anhydride or separating it as a solution is preferred, since the purification of tetrafluorophthalic acid, which is the desired product, can be easily performed and high-purity tetrafluorophthalic acid can be obtained.

In addition, in the process of this invention, the N-substituted tetrafluorophthalimide which is hydrolyzed in the second step may be or may not be isolated in the first step.

Tetrafluorophthalic acid is a useful compound as basic starting material for the manufacture of medicaments, agricultural chemicals, and other industrial products. For example, it is very useful as a starting material for producing fluorine-containing pyridonecarboxylic acid series synthetic antibacterial agents.

Thus, tetrafluorophthalic acid, which is a useful compound in various fields, can be advantageously produced on an industrial scale by the process of this invention.

That is, according to the process of this invention, tetraflurophthalic acid can be produced with good yield by the reaction in two steps using the imide compound represented by formula (I) or (II) described above as a starting material, and these reactions can be industrially practiced.

The following examples are intended to illstrate specific embodiments of the present invention, but are not to be construed as limiting it in any way. Unless otherwise indicated, all parts, percents and ratios are by weight.

EXAMPLE 1

Synthesis of N-methyl-tetrafluorophthalimide (Process using sulfolane as solvent)

(1) In a 500 ml three neck distillation flask was placed 350 ml of sulfolane and then about 50 ml thereof was distilled off under a reduced pressure at 120°~130° C. Thereafter, 59.8 g (0.2 mol) of N-methyltetrachlorophthalimide, 69.6 g (1.2 mols) of spray-dried potassium fluoride, and 7 g of tetraphenylphosphonium bromide were added thereto and they were reacted for 3 hours at 140° to 150° C. with stirring. After cooling, the reaction mixture was poured into 500 ml of ethyl acetate and the mixture was washed three times with 2 l of an aqueous 10% sodium chloride solution. An organic layer separated therefrom was dried using anhydrous magnesium sulfate, and then the ethyl acetate was removed by distillation, whereby 40 g (yield 85.5%) of N-methyl-tetrafluorophthalimide was obtained as brown crystals, which was analyzed as follows:

$^{19}F$ NMR (ppm/acetone, external standard $CF_3CO_2H$): 60, 67(d-d, each 2F, $J_{FF}$=7.9, 18.22 Hz).

$^1H$ NMR (ppm/$CDCl_3$): 3.12(s).

IR ($cm^{-1}$/KBr): $\nu_{C=O}$ 1705.

(2) The same procedure as the above process (1) was followed while changing the reaction time and reaction temperature. Each reaction mixture obtained was analyzed by gas chromatography (column temperature 220° C.) packed with OV-1 (methyl silicone, produced by Nishio Kogyo Co.) to determine the area percentage of N-methyltetrafluorophthalimide according to areametric analysis (i.e., ratio of the area corresponding to the N-substituted tetrafluorophthalimide eluted to the area corresponding to the whole reaction mixture (excluding solvent) eluted). The results obtained are shown in Table 1.

TABLE 1

| Reaction temperature | N—Methyl-Tetrafluorophthalmide (%) Reaction time | | | |
|---|---|---|---|---|
| | 0.5 hr. | 1 hr. | 2 hrs. | 3 hrs. |
| 120–130° C. | 8.3 | 35.4 | 87.5 | 94.3 |
| 130–140° C. | 11.0 | 47.2 | 89.0 | 95.2 |
| 140–150° C. | 63.2 | 93.2 | 95.0 | |
| 150–160° C. | 81.5 | 93.0 | 96.5 | |
| 160–170° C. | 93.0 | 95.2 | | |
| 170–180° C. | 94.2 | 95.3 | | |
| 180–200° C. | 95.2 | | | |

(3) The same procedure as the above process (1) was followed while changing the reaction time and the kind and amount of catalyst used, and each of the reaction mixture obtained was measured as in the above process (2). The results obtained are shown in Table 2 below.

TABLE 2

| Catalyst* | N—methyl-Tetrafluorophthalimide (%) Reaction time (hrs.) | | | | | | | |
|---|---|---|---|---|---|---|---|---|
| | 0.5 | 1 | 2 | 3 | 5 | 7 | 8 | 10 |
| none | 0.5 | 21.6 | 40.5 | 61.2 | 78.3 | 89.7 | 92.5 | 96.5 |
| A, 1% | 9.6 | 35.8 | 65.2 | 74.0 | 86.0 | 93.3 | 97.0 | |
| A, 5% | 55.5 | 80.9 | 96.7 | | | | | |
| A, 10% | 84.0 | 96.5 | | | | | | |
| B, 5% | 85.3 | 95.5 | | | | | | |
| B, 10% | 86.1 | 96.5 | | | | | | |
| C, 5% | 46.4 | 64.2 | 85.6 | 91.2 | 97.8 | | | |
| C, 10% | 88.5 | 96.6 | | | | | | |

[Notes]
*A: Tetraphenylphosphonium bromide
*B: Tetra-n-butylammonium bromide
*C: Trioctylmethylammonium chloride
Catalyst amount (%) is shown by mol % based on N—methyl-tetrachlorophthalimide (4) The same procedure as the above process (1) was followed while changing the amount of spray-dried potassium fluoride to 0.8 mol, 1.0 mol, and 1.2 mols, respectively. When each of the reaction mixtures obtained was measured as in the above (2), the area percentage of N-methyltetrafluorophthalimide was 90%, 94%, and 95%, respectively.

(5) In a 300 ml three neck distillation flask was place 200 ml of sulfolane and about 50 ml thereof was distilled off under a reduced pressure. Thereafter, 29.9 g (0.1 mol) of N-methyl-tetrachlorophthalimide, 34.8 g (0.6 mol) of spray-dried potassium fluoride, and 2.01 g (0.005 mol) of trioctylmethylammonium chloride were added thereto and they were reacted with stirring for 2 hours at 120° to 130° C. and further for 2 hours at 140° to 150° C.

After cooling, the reaction mixture was poured into 500 ml of toluene, washed four times with 600 ml of an aqueous sodium chloride solution, and an organic layer thus formed was recovered and dried using anhydrous magnesium sulfate. The organic layer was then concentrated by distillation under a reduced pressure to provide 19.8 g (yield 85%) of N-methyl-tetrafluorophthalimide as yellow-brown crystals.

(6) In a 200 ml three neck distillation flask was place 150 ml of sulfolane and about 30 ml thereof was distilled off under a reduced pressure. Thereafter, 15 g (0.05 mol) of N-methyl-tetrachlorophthalimide and 17.4 g (0.3 mol) of spray-dried potassium fluoride were added thereto and they were reacted for 10 hours at 150° to 160° C. with stirring. After cooling, the reaction mixture was poured into 300 ml of toluene, washed three times with 600 ml of an aqueous sodium chloride solution, and dried with anhydrous magnesium sulfate. Then, the reaction mixture was concentrated by distillation under a reduced pressure to provide 9.7 g (yield 83%) of N-methyl-tetrafluorophthalimide as yellow-brown crystals.

(7) In a 300 ml three neck distillation flask was placed 150 ml of sulfolane and about 30 ml thereof was distilled off under a reduced pressure. Thereafter, 29.9 g (0.1 mol) of N-methyl-tetrachlorophthalimide, 34.8 g (0.6 mol) of spray-dried potassium fluoride, and 1.6 g (0.005 mol) of tetra-n-butylammonium bromide were added thereto and the mixture was reacted for 2 hours at 150° to 160° C. with stirring. After cooling, the reaction mixture was poured to 500 ml of toluene, washed three times with 1 l of an aqueous sodium chloride solution, and dried with anhydrous magnesium sulfate. Then, the reaction mixture was concentrated by distillation under a reduced pressure to provide 21.0 g (yield 90%) of N-methyl-tetrafluorophthalimide as yellow-brown crystals.

EXAMPLE 2

Synthesis of N-methyl-tetrafluorophthalimide (Process without solvent)

In a 300 ml three neck distillation flask were placed 12 g (0.04 mol) of N-methyl-tetrachlorophthalimide, 14 g (0.24 mol) of spray-dried potassium fluoride, and 1.4 g of tetraphenylphosphonium bromide, and the mixture was reacted on an oil bath with stirring for 2 hours at 150° to 160° C. and further for 2 hours at 190° to 200° C. After cooling, the reaction mixture was extracted with 250 ml of toluene and after removing inorganic matter by filtration, the filtrate thus formed was washed three times with 50 ml of an aqueous sodium chloride solution, dried with anhydrous magnesium sulfate, and concentrated to provide 8.5 g (yield 80%) of N-methyl-tetrafluorophthalimide as yellow-brown crystals.

EXAMPLE 3

Hydrolysis of N-methyl-tetrafluorophthalimide (1) Synthesis of anhydrous tetrafluorophthalic anhydride:

In a 500 ml three neck distillation flask were placed 38 g (0.16 mol) of N-methyl-tetrafluorophthalimide, 38 ml of concentrated sulfuric acid, 12 ml of water, and 38 ml of acetic acid, and the mixture was reacted for 6 hours at 150° C. with stirring. After cooling, the reaction mixture was extracted three times with 200 ml of toluene, and the toluene layers were combined and concentrated by distillation under a reduced pressure to provide 28 g of faint brown crystals. By distilling the residue thus formed under a reduced pressure (14 mmHg) at 138° C., 21 g (yield 59.6%) of tetrafluorophthalic anhydride was obtained as white crystals. The analysis of the product was as follows:

$^{19}F$ NMR (ppm/acetone, external standard $CF_3CO_2H$): 63, 69(d-d, each 2F, $J_{FF}$=10.35, 19.26, Hz).

(2) Synthesis of tetrafluorophthalic acid:

After mixing 10 g (0.945 mol) of tetrafluorophthalic anhydride obtained in the above step with 60 ml of water, the mixture was stirred for 3 hours at room temperature. Then, the product was extracted twice with 300 ml of ether and the ether layer thus obtained was dried with anhydrous magnesium sulfate and concentrated by distillation to provide 9.7 g (yield 90%) of tetrafluorophthalic acid as white crystals. By recrystallizing the crystals from an aqueous 6N hydrochloric acid solution, crystals having higher purity (99.5%) were obtained.

EXAMPLE 4

Synthesis of N-ethyl-tetrafluorophthalimide (Process using sulfolane as solvent)

In a 1 l three neck distillation flask was placed 500 ml of sulfolane and about 100 ml thereof was distilled off under a reduced pressure. Thereafter 93.9 g (0.3 mol) of N-ethyl-tetrachlorophthalimide, 104.4 g (1.8 mols) of spray-dried potassium fluoride, and 10.4 g of tetraphenylphosphonium bromide were added thereto and they were reacted for 2 hours at 150° to 160° C. with stirring. After cooling, the reaction mixture was poured into 500 ml of toluene, washed three times with 2 l of an aqueous sodium chloride solution, dried with anhydrous magnesium sulfate, and concentrated by distillation under a reduced pressure to provide 56 g (yield 75.6%) of N-ethyl-tetrafluorophthalimide as yellow ocher-color crystals. The analysis of the product was as follows:

$^{19}F$ NMR (ppm/acetone, external standard $CF_3CO_2H$): 60, 67(d-d, each 2F, $J_{FF}$=8.09, 19.76 Hz).

$^1H$ NMR (ppm/$CDCl_3$): 1.26(3H, t, J=8 Hz),. 3.68(2H, q, J=8 Hz)

IR ($cm^{-1}$/KBr): $\nu_{C=O}$ 1700.

EXAMPLE 5

Synthesis of N-ethyl-tetrafluorophthalimide (Process without solvent)

In a 300 ml three neck distillation flask were placed 31.3 g (0.1 mol) of N-ethyl-tetrachlorophthalimide, 34.8 g (0.6 mol) of spray-dried potassium fluoride and 3.5 g of tetraphenylphosphonium bromide, and they were reacted for 2 hours on an oil bath at 180° C. with stirring. After cooling, the reaction mixture was extracted with the addition of 150 ml of toluene, and after removing inorganic matter by filtration, the toluene layer formed was washed three times with 100 ml of an aqueous sodium chloride solution, dried with anhydrous magnesium sulfate, and concentrated to provide 22.8 g (yield 92.3%) of N-ethyl-tetrafluorophthalimide as yellow-brown crystals.

EXAMPLE 6

Hydrolysis of N-ethyl-tetrafluorophthalimide (1) Synthesis of tetrafluorophthalic anhydride:

In a 500 ml three neck distillation flask were placed 49.4 g (0.2 mol) of N-ethyl-tetrafluorophthalimide, 74 ml of concentrated sulfuric acid, 50 ml of acetic acid, and 15 ml of water, and the mixture was reacted for 5 hours at 140° to 150° C. with stirring. After cooling, the reaction mixture was extracted three times with 200 ml of toluene, and the toluene layers were collected and concentrated by distillation under a reduced pressure to provide 35 g of faint brown crystals. By distilling the residue thus formed under a reduced pressure (19 mmHg) at 140° C., 26.8 g (yield 60.9%) of tetrafluorophthalic anhydride was obtained as white crystals.

(2) Synthesis of tetrafluorophthalic acid:

After mixing 110 g (0.5 mol) of tetrafluorophthalic anhydride and 150 ml of water, the mixture was refluxed for about one hour. After cooling the reaction mixture, crystals deposited were collected by filtration and dried to provide 97.6 g (yield 82%) of tetrafluorophthalic acid as white crystals. If necessary, the crystals could be further purified by recrystallization from an aqueous 6N hydrochloric acid solution.

EXAMPLE 7

Synthesis of N-isopropyl-tetrafluorophthalimide (Process using sulfolane as solvent)

In a 1 l three neck distillation flask was placed 500 ml of sulfolane and then about 100 ml thereof was distilled off under a reduced pressure. Thereafter, 81.8 g (0.25 mol) of N-isopropyl-tetrachlorophthalimide, 87 g (1.5 mols) of spray-dried potassium fluoride, and 8.7 g of tetraphenylphosphonium bromide were added thereto and they were reacted for 3 hours at 140° to 150° C. with stirring. After cooling, the reaction mixture was poured into 500 ml of toluene, washed three times with 2 l of an aqueous sodium chloride solution, dried with anhydrous magnesium sulfate, and concentrated by distillation under a reduced pressure to provide 56 g (yield 75.6%) of N-isopropyl-tetrafluorophthalimide as yellow ocher-color crystals, analyzed as follows:

$^{19}F$ NMR (ppm/acetone, external standard $CF_3CO_2H$): 61, 67(d-d, each 2F, $J_{FF}$=7.71, 18.91 Hz).

$^1H$ NMR (ppm/$CDCl_3$): 1.46(6H, d, J=7 Hz), 4.44(1H, hep, J=7 Hz).

EXAMPLE 8

Synthesis of N-isopropyl-tetrafluorophthalimide (Process without solvent)

In a 300 ml three neck distillation flask were placed 32.7 g (0.1 mol) of N-isopropyl-tetrachlorophthalimide, 34.8 g (0.6 mol) of spray-dried potassium fluoride and 3.5 g of tetraphenylphosphonium bromide, and they were reacted with stirring for 30 minutes at 160° to 170° C. and further for 2 hours at 190° to 200° C. After cooling, the reaction mixture was extracted with the addition of 150 ml of toluene, and after removing inorganic matter by filtration, the toluene layer was washed three times with 100 ml of an aqueous sodium chloride solution, dried by anhydrous magnesium sulfate, and concentrated by distillation under a reduced pressure to provide 24.9 g (yield 95.4%) of N-isopropyl-tetrafluorophthalimide as yellow-brown crystals.

EXAMPLE 9

Hydrolysis of N-isopropyl-tetrafluorophthalimide (1) Synthesis of tetrafluorophthalic anhydride:

In a 500 ml three neck distillation flask were placed 47 g (0.18 mol) of N-isopropyl-tetrafluorophthalimide, 71 ml of concentrated sulfuric acid, 43 ml of acetic acid, and 13 ml of water, and the mixture was reacted for 5 hours at 140° to 150° C. with stirring. After cooling, the reaction mixture was extracted three times with 200 ml of toluene, and the toluene layers thus formed were collected and concentrated by distillation under a reduced pressure to provide 26.3 g (yield 66.4%) of tetrafluorophthalic anhydride as white crystals.

(2) Synthesis of tetrafluorophthalic acid:

The crude crystals obtained by the above process (1) were reacted as in Example 6-(2) and after distilling off water from the reaction mixture at 80° C. under a reduced pressure, the product was dried to provide tetrafluorophthalic acid as crystals.

EXAMPLE 10

Synthesis of N-cyclohexyl-tetrafluorophthalimide

After mixing 73.4 g (0.2 mols) of N-cyclohexyltetrachlorophthalimide, 69.6 g (1.2 mols) of dried potassium fluoride, and 7 g of tetraphenylphosphonium bromide with 300 ml of anhydrous sulfolane, the mixture was reacted with stirring for 3 hours at 180° C. After the reaction was completed, the reaction mixture obtained was cooled and after removing inorganic matter by filtration, the filtrate formed was poured into water to provide yellow crystals, which were dried and then used for the following reaction.

EXAMPLE 11

Hydrolysis of N-cyclohexyl-tetrafluorophthalimide

After mixing 50 g of the above dried N-cyclohexyltetrafluorophthalimide with 80 ml of 85% sulfuric acid, 80 ml of acetic acid was added to the mixture and it was reacted for 5 hours at 120° C. to 130° C. with stirring. After the reaction was completed, acetic acid was distilled off from the reaction mixture under a reduced pressure and the product was continuously extracted with toluene for 24 hours. When the toluene layer obtained was concentrated by distillation under a reduced pressure, crude crystals of yellow tetrafluorophthalic anhydride were precipitated. The concentrate was distilled under a reduced pressure (20 mmHg) at 150° C. and the crystals thus obtained were hydolyzed by adding 100 ml of an aqueous 6N hydrochloric acid solution. The hydrolyzed product was cooled and then extracted with ether to provide white crystals of tetrafluorophthalic acid (yield 90%).

EXAMPLE 12

Synthesis of N-benzyl-tetrafluorophthalimide

In a 300 ml three neck distillation flask were placed 200 ml of sulfolane and then about 50 ml thereof was distilled off under a reduced pressure. Thereafter, 75 g (0.2 mol) of N-benzyltetrachlorophthalimide, 69.6 g (1.2 mols) of spray-dried potassium fluoride, and 4.2 g (0.01 mol) of tetraphenylphosphonium bromide were added thereto and the mixture was reacted for one hour at 150° to 160° C. with stirring. After cooling, the reaction mixture was poured into 400 ml of toluene, and the toluene layer formed was washed four times with 400 ml of an aqueous sodium chloride solution, dried with anhydrous magnesium sulfate, and concentrated by distillation under a reduced pressure to provide 55 g (yield 89%) of N-benzyltetrafluorophthalimide as grey crystals, analyzed as follows:

$^{19}$F NMR (ppm/ethyl acetate, external standard $CF_3CO_2H$): 59.3, 66.7(d-d, each 2F, $J_{FF}=8.47$, 19.76 Hz).

$^1$H NMR (ppm/CDCl$_3$): 4.72 (s, 2H), 7.05 to 7.45(m, 5H).

IR (cm$^{-1}$/KBr) $\nu_{C=O}$ 1705.

EXAMPLE 13

After mixing 361 g (1 mol) of N-phenyltetrachlorophthalimide as prepared in Reference Example set forth below, 348 g (6 mols) of fine particulate potassium fluoride (diameter: 10–50 μm; specific surface area (BET method): 1.0–2.0 m$^2$/g; "CLOCAT F", trade name, made by Morita Kagaku K.K.), and 17.4 g (0.04 mol) of tetraphenylphosphonium bromide in 1 l of anhydrous sulfolane, the mixture was stirred for 3 hours at 150° C. After cooling the reaction mixture, inorganic matter was removed by filtration and the filtrate thus formed was poured in water to precipitate crystals, which were collected by filtration and dried to provide 265 g (yield 90%) of yellow crystals of N-phenyltetrafluorophthalimide.

Then, 29.5 g (0.1 mol) of the N-phenyltetrafluorophthalimide described above was mixed with 60 ml of 90% sulfuric acid and the mixture was stirred for 3 hours at 110° C. After cooling, the reaction mixture was poured into 120 g of crushed ice and extracted three times with 500 ml of ether. The ether layers thus obtained were collected, dried with anhydrous magnesium sulfate, and concentrated by distillation to provide 16.9 g (yield 71%) of tetrafluorophthalic acid as white crystals having a melting point of from 148° C. to 152° C., analyzed as follows:

$^{19}$F NMR (ppm/acetone, external standard $CF_3CO_2H$): 58.5, 71(d-d, each 2F, each $J_{FF}=13.56$ Hz).

A part of the white crystals obtained was recrystallized from an aqueous 6N hydrochloric acid solution and subjected to elemental analysis, with the following results:

|  | C | F |
| --- | --- | --- |
| Calculated | 40.3% | 31.9% |
| Found | 40.7% | 32.1% |

EXAMPLE 14

After mixing 361 g (1 mol) of N-phenyltetrachlorophthalimide, 348 g (6 mols) of fine particulate potassium fluoride particle diameter (CLOCAT F), and 17.4 g (0.04 mol) of tetraphenylphosphonium bromide, the mixture was stirred on an oil bath at 220° C. to 230° C. for 4 hours. After cooling, toluene was added to the reaction mixture and after removing inorganic matter by filtration, the filtrate formed was concentrated by distillation under a reduced pressure to provide 271 g (yield 92%) of yellow crystals of N-phenyltetrafluorophthalimide.

Then, 29.5 g (0.1 mol) of N-phenyltetrafluorophthalimide described above was mixed with 70 ml of 80% sulfuric acid and the mixture was stirred for 10 hours at 100° C. After cooling, the reaction mixture was poured into 110 g of ice-water and extracted three times with 500 ml of dichloromethane. The dichloromethane layers thus formed were collected, washed once with an aqueous sodium chloride solution, dried with anhydrous magnesium sulfate, and concentrated by distillation under a reduced pressure to provide 15.5 g (yield 65%) of tetrafluorophthalic acid.

EXAMPLE 15

After mixing 198 g (0.5 mol) of N-(p-chlorophenyl) tetrachlorophthalimide, 174 g (3.0 mols) of fine particulate potassium fluoride purified, produced by Riedel-deHaen Co., and 1.5 g of 18-crown-6 with 500 ml of anhydrous sulfolane, the mixture was stirred for 3 hours at 150° C. After cooling the reaction mixture, inorganic matter was removed therefrom by filtration, the filtrate thus obtained was poured into water to precipitate crystals, which were collected by filtration and dried to provide 147 g of yellow crystals.

Then, 33 g of these yellow crystals were mixed with 60 ml of 90% sulfuric acid, and mixture was stirred for 3 hours at 110° C. After cooling, the reaction mixture was poured into 120 g of water and extracted three times with 500 ml of ether. The ether layers formed were collected, dried with anhydrous magnesium sulfate, and concentrated by distillation to provide 19 g of tetrafluorophthalic acid as crude crystals. When the crude crystals were recrystallized from an aqueous 6N hydrochloric acid solution, 16.2 g (yield 68%) of white crystals having a melting point of 152° C. to 153° C. were obtained.

EXAMPLE 16

After mixing 73.4 g of N,N'-methylene-bis[4-(tetrachlorophthalimido)phenyl], 58 g of fine particulate potassium fluoride (CLOCAT F), and 3.29 g of tetrabutylammonium tetrafluoroborate with 700 ml of anhydrous sulfolane, the mixture was heated at 125°~135° C. with stirring to distill off 90 ml of anhydrous sulfolane. Thereafter, the mixture was stirred for 6 hours at 150° C. After cooling, inorganic matter was removed therefrom by filtration, the inorganic matter was washed with 100 ml of toluene, and the resulting washing solution was combined with the filtrate. The mixture thus formed was concentrated by distillation under a reduced pressure and the residue formed was used for the following reaction without being isolated and purified.

This residue was mixed with 120 ml of 95% sulfuric acid and the mixture was stirred for 5 hours at 140 to 150° C. After cooling, the reaction mixture was extracted three times with 200 ml of toluene, the organic layers formed were collected and concentrated by distillation under a reduced pressure. The residue thus formed was dissolved in 200 ml of water and the solution was refluxed for one hour. The reaction mixture thus obtained was concentrated by distillation under a reduced pressure to provide 41.4 g of crude crystals. The tetraphthalic acid content of the crude crystals was analyzed by liquid chromatography using an absolute calibration curve to determine the yield thereof, which was 60.5%.

EXAMPLE 17

After mixing 89.4 g of N,N'-dimethylenebis(tetrachlorophthalimide), 87 g of fine particulate potassium fluoride (CLOCAT F), and 6.3 g of tetraphenylphosphonium bromide with 400 ml of anhydrous sulfolane, the mixture was reacted and analyzed as in Example 16 described above. The yield of tetraflurophthalic acid obtained was 46.0%.

EXAMPLE 18

After mixing 55.3 g of N-allyl-tetrachlorophthalimide, 49.3 g of fine particulate potassium fluoride (CLOCAT F), and 2.8 g of tetrabutylammonium tetrafluoroborate with 300 ml of anhydrous sulfolane, the mixture was stirred with heating (110°~120° C.) to distill off 30 ml of anhydrous sulfolane, and thereafter, the resultant mixture was stirred for 7 hours at 150° to 170° C. After cooling, the reaction mixture was extracted with 500 ml of toluene and the extract was washed 6 times with 500 ml of water, dried with anhydrous magnesium sulfate, and after filtration, the toluene was distilled off from the filtrate under a reduced pressure to provide 42.6 g of N-ally-tetrafluorophthalimide as crude crystals (purity 95.0%).

Then, 42.0 of these crude crystals was mixed with 70 ml of 92% sulfuric acid, and the mixture was stirred for 2 hours at 150° C. After cooling, the reaction mixture was extracted three times with 200 ml of toluene and the extract was treated as in Example 9-(1) to provide 38 g of tetrafluorophthalic anhydride (purity 95.2%).

By further reacting the tetrafluorophthalic anhydride thus obtained as in Example 9-(2), it would be possible to obtain tetrafluorophthalic acid.

EXAMPLE 19

After mixing 53.9 g of N-phenyl-tetrabromophthalimide, 29 g of fine particulate potassium fluoride (CLOCAT F), and 2.1 g of tetraphenylphosphonium bromide with 300 ml of anhydrous sulfolane, the mixture was stirred at 130°~140° C. to distill off 30 ml of anhydrous sulfolane. Thereafter, the resultant mixture was stirred for 8.5 hours at 150° to 170° C. After cooling, the reaction mixture was treated with toluene as in Example 12 to provide 26.07 g of crystals of N-phenyl-tetrafluorophthalimide (purity 95.9%).

EXAMPLE 20

The reaction was performed using the same reagents as in Example 19, except that anhydrous sulfolane (solvent) was not used and the reaction was performed at 190° to 200° C. for 6 hours with stirring. As a result, 28.1 g of N-phenyl-tetrafluorophthalimide crystals were obtained (purity 94.1%).

REFERENCE EXAMPLE

Synthesis of N-phenyltetrachlorophthalimide used in Example 13

In 1.2 l of dioxane was dissolved 286 g (1 mol) of tetrachlorophthalic anhydride, and while refluxing the solution, 93 g (1 mol) of aniline was added dropwise to the solution. Thereafter, the mixture was refluxed for 2 hours. The reaction mixture was allowed to cool, whereby tabular crystals were precipitated. The crystals were collected by filtration, washed with dioxane, and dried to provide 325 g of N-phenyltetrachlorophthalimide having a melting point of 251° C. to 253° C. (yield 90%).

While the invention has been described in detail and with reference to specific embodiments thereof, it will be apparent to one skilled in the art that various changes and modifications can be made therein without departing from the spirit and scope thereof.

What is claimed is:

1. A process for producing tetrafluorophthalic acid, which comprises the steps of
   (a) reacting an alkali metal fluoride and at least one imide compound represented by formula (I) or (II)

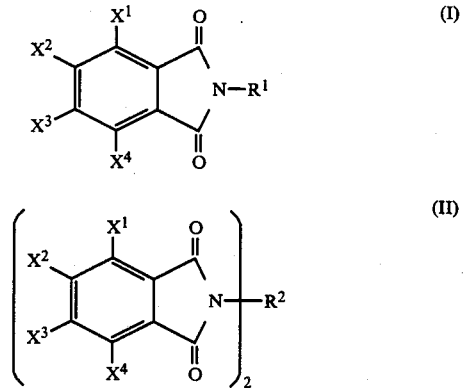

wherein $X^1$, $X^2$, $X^3$, and $X^4$, which may be the same or different, each represents a chlorine atom or a bromine atom, $R^1$ represents a monovalent organic group, and $R^2$ represents a divalent organic group; to provide an N-substituted tetrafluorophthalimide; and
   (b) hydrolyzing said tetrafluorophthalimide in the presence of an acid.

2. The process for producing tetrafluorophthalic acid as claimed in claim 1, further comprising steps of
   (c) isolating tetrafluorophthalic anhydride or separating a solution of tetrafluorophthalic anhydride from the reaction mixture after step (b); and
   (d) hydrolyzing said tetrafluorophthalic anhydride.

3. The process for producing tetrafluorophthalic acid as claimed in claim 1, wherein said alkali metal fluoride is potassium fluoride.

4. The process for producing tetrafluorophthalic acid as claimed in claim 1, wherein the reaction of said imide compound and said fluoride in step (a) is conducted in the presence of a phase transfer catalyst.

5. The process for producing tetrafluorophthalic acid as claimed in claim 4, wherein said catalyst is selected from the group consisting of a quaternary ammonium salt, a quaternary phosphonium salt, and a cyclic polyether.

6. The process for producing tetrafluorophthalic acid as claimed in claim 5, wherein said quaternary ammonium salt is a tetraalkylammonium halide, a tetraalkylammonium tetrafluoroborate, or a tetraalkylammonium phosphorustetrafluoride.

7. The process for producing tetrafluorophthalic acid as claimed in claim 5, wherein said quaternary phosphonium salt is an alkyltriphenylphosphonium halide or a tetraphenylphosphonium halide.

8. The process for producing tetrafluorophthalic acid as claimed in claim 5, wherein said cyclic polyether is 18-crown-6, dibenzo-18-crown-6, or dicyclohexano-crown-6.

9. The process for producing tetrafluorophthalic acid as claimed in claim 1, wherein said imide compound and said alkali metal fluoride in step (a) are reacted in an aprotic polar solvent at a temperature of from about room temperature to 250° C.

10. The process for producing tetrafluorophthalic acid as claimed in claim 1, wherein said monovalent organic group represented by $R^1$ is a straight chain or branched chain alkyl group having from 1 to 8 carbon atoms, a cycloalkyl group having from 3 to 8 carbon atoms, an alkenyl group having from 3 to 8 carbon atoms, an aryl group, or a heterocyclic group; and said divalent hydrocarbon group represented by $R^2$ is a straight chain or branched chain alkylene group having from 1 to 8 carbon atoms, a cycloalkylene group having from 3 to 8 carbon atoms, an alkenylene group having from 3 to 8 carbon atoms, an arylene group, a divalent hetrocyclic group, or $-R^3-R^4-R^5-$, wherein $R^3$ and $R^5$ each represents a straight chain or branched chain alkylene group having from 1 to 8 carbon atoms, a cycloalkylene group having from 3 to 8 carbon atoms, an alkenylene group having from 3 to 8 carbon atoms, an arylene group, or a divalent heterocyclic group, and $R^4$ represents those defined for $R^3$ and $R^5$ and further represents $-O-$, $-S-$, $-SO-$, $-SO_2-$, or

wherein $R^6$ represents an alkyl, cycloalkyl, alkenyl, aryl, or hetrocyclic group as defined for $R^1$, provided that all of $R^3$, $R^4$ and $R^5$ are not alkylene groups, cycloalkylene groups, alkenylene groups, or arylene groups.

11. The process for producing tetrafluorophthalic acid as claimed in claim 10, wherein the group represented by $R^1$ or $R^2$ is substituted with a substituent selected from the group consisting of a halogen atom, a straight or branched chain alkyl group having from 1 to 8 carbon atoms, a cycloalkyl group having from 3 to 8 carbon atoms, an alkenyl group having from 3 to 8 carbon atoms, an aryl group, a cyano group, a nitro group, $R^7O-$, $R^8S-$, $R^8SO-$, $R^8SO_2-$, and

wherein $R^7$, $R^8$, $R^9$, and $R^{10}$ each represents those defined for $R^1$.

12. The process for producing tetrafluorophthalic acid as claimed in claim 1, wherein $R^1$ represents a methyl group, an ethyl group, a propyl group, an isopropyl group, a butyl group, an isobutyl group, a secbutyl group, a tert-butyl group, a pentyl group, a hexyl group, a 2-ethylhexyl group, an octyl group, a cyclopentyl group, a cyclohexyl group, a benzyl group, a p-chlorobenzyl group, a p-methylbenzyl group, an allyl group, a phenyl group, a p-chlorophenyl group, a p-bromophenyl group, a p-fluorophenyl group, a p-tolyl group, a 2,4-dichlorophenyl group, a 3,4-dichlorophenyl group, a 2-chloro-4-methylphenyl group, a 2,4-xylyl group, a p-ethoxyphenyl group, an m-methylthiophenyl group, a p-(p-chlorophenoxy)phenyl group, a p-(benzenesulfonyl)phenyl group, a 1-naphthyl group, a 2-naphthyl group, a 2-thienyl group, a 2-methoxyethyl group, a 2-(dimethylamino)ethyl group, a 3-[4-(dimethylamino)phenyl]propyl group, a (3,5-dimethyl-4-isoxazolyl)methyl group, a 3-(4-methoxyphenyl)-butyl group, a 3-(4-methoxyphenyl)propyl group, a 6-methyl-2-pyridyl group, a 4-methoxy-2-methylphenyl group, a 3-methoxypropyl group, a 1-methyl-2-phenylethyl group, a 2,3,5,6-tetrafluoro-4-pyridyl group, a 2-phenoxyethyl group, a 4-nitrophenyl group, a 4-cyanophenyl group, a 2,6-dimethyl-4-pyrimidyl group, a 2-morpholinoethyl group, an α,α,α-trifluoro-o-tolyl group, a 2-(2-pyridyl)ethyl group, or a 3-pyridyl group; $R^2$ represents —CH$_2$CH$_2$—,

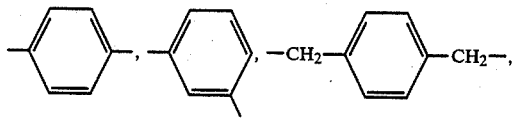

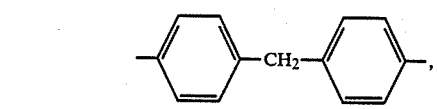

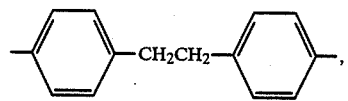

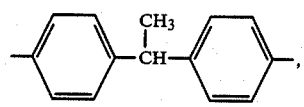

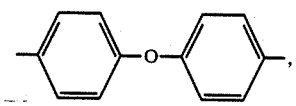

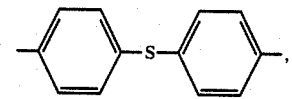

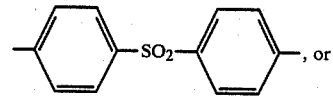

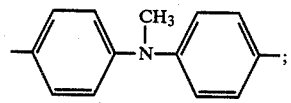

and $X^1$, $X^2$, $X^3$, and $X^4$ all represent the same element.

13. The process for producing tetrafluorophthalic acid as claimed in claim 9, wherein said solvent is sulfolane and said reaction is conducted at a temperature of from about 80° to 220° C., for a period of from about 0.2 to 72 hours.

14. The process for producing tetrafluorophthalic acid as claimed in claim 13, wherein said temperature is from about 120° to 220° C., for a period of from about 0.5 to 36 hours.

15. The process for producing tetrafluorophthalic acid as claimed in claim 1, wherein said imide compound is represented by formula (I) and said alkali metal fluoride is present in an amount of from about 4.0 to 12.0 mols per mol of said imide compound.

16. The process for producing tetrafluorophthalic acid as claimed in claim 1, wherein said imide compound is represented by formula (II) and said alkali metal fluoride is present in an amount of from about 8.0 to 24.0 mols per mol of said imide compound.

17. The process for producing tetrafluorophthalic acid as claimed in claim 3, wherein said imide compound is represented by formula (I) and said potassium fluoride is present in an amount from about 4.1 to 8.0 mols per mol of said imide compound.

18. The process for producing tetrafluorophthalic acid as claimed in claim 3, wherein said imide compound is represented by formula (II) and said potassium fluoride is present in an amount of from about 8.2 to 16.0 mols per mol of said imide compound.

19. The process for producing tetrafluorophthalic acid as claimed in claim 5, wherein the amount of said catalyst is from about 0.00001 to 0.6 mol per mol of said imide compound.

20. The process for producing tetrafluorophthalic acid as claimed in claim 19, wherein the amount of said catalyst is from about 0.001 to 0.3 mol per mol of said imide compound.

21. The process for producing tetrafluorophthalic acid as claimed in claim 1, wherein said acid is present in an amount of from about 0.5 to 48 mols per mol of said imide compound.

22. The process for producing tetrafluorophthalic acid as claimed in claim 1, wherein said acid is sulfuric acid having a concentration of from about 30 to 98 wt %.

23. A process for producing tetrafluorophthalic acid which comprises the steps of:
(a) reacting an alkali metal fluoride and at least one imide compound represented by formula (I) or (II)

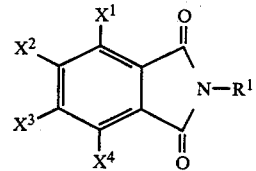 (I)

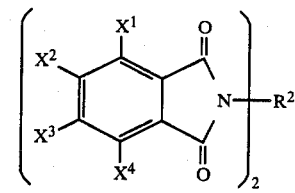 (II)

wherein $X^1$, $X^2$, $X^3$, and $X^4$, which may be the same or different, each represents a chlorine atom or a bromine atom, $R^1$ represents a monovalent organic group, and $R^2$ represents a divalent organic group, to provide an N-substituted tetrafluorophthalimide;
(b) hydrolyzing said tetrafluorophthalimide in the presence of an acid;
(c) extracting said hydrolyzed product with an aprotic solvent to provide tetrafluorophthalic anhydride; and
(d) hydrolyzing said tetrafluorophthalic anhydride to provide tetrafluorophthalic acid.

24. The process for producing tetrafluorophthalic acid as claimed in claim 23, wherein said tetrafluorophthalic anhydride is purified prior to said hydrolysis step (d).

25. The process for producing tetrafluorophthalic acid as claimed in claim 1, wherein said step (b) is conducted at a temperature of from about 70° to 200° C. but below a refluxing temperature for a period of from about 0.5 to 72 hours.

26. The process for producing tetrafluorophthalic acid as claimed in claim 25, wherein said step (b) is conducted at a temperature of from about 110° to 200° C. at a pressure of from about 1 to 15 kg/cm² for a period of from about 0.5 to 36 hours.

* * * * *